(12) United States Patent
Morrow et al.

(10) Patent No.: US 6,804,610 B2
(45) Date of Patent: Oct. 12, 2004

(54) INDIRECT MEASUREMENT OF NITROGEN IN A MULTI-COMPONENT GAS BY MEASURING THE SPEED OF SOUND AT TWO STATES OF THE GAS

(75) Inventors: Thomas B. Morrow, San Antonio, TX (US); Kendricks A. Behring, II, Torrance, CA (US)

(73) Assignee: Southwest Research Institute, San Antonio, TX (US)

( * ) Notice: Subject to any disclaimer, the term of this patent is extended or adjusted under 35 U.S.C. 154(b) by 21 days.

(21) Appl. No.: 10/401,206

(22) Filed: Mar. 27, 2003

(65) Prior Publication Data

US 2003/0212496 A1 Nov. 13, 2003

Related U.S. Application Data

(63) Continuation-in-part of application No. 09/550,431, filed on Apr. 17, 2000, now Pat. No. 6,604,051.

(51) Int. Cl.[7] .............................................. G01N 31/00
(52) U.S. Cl. ........................................ 702/24; 73/23.2
(58) Field of Search .............................. 702/24, 23, 50; 703/23.2, 597, 861.04, 24.05, 25.01; 110/238; 261/76; 75/708; 436/133; 426/450

(56) References Cited

U.S. PATENT DOCUMENTS

| 4,489,592 | A |   | 12/1984 | Pacanowski et al. ........... 73/30 |
| 4,596,133 | A |   | 6/1986 | Smalling et al. ................ 73/24 |
| 5,285,675 | A |   | 2/1994 | Colgate et al. .............. 73/23.2 |
| 5,311,447 | A | * | 5/1994 | Bonne .......................... 702/50 |
| 5,486,107 | A |   | 1/1996 | Bonne .......................... 431/12 |
| 5,537,854 | A |   | 7/1996 | Phillips et al. ............. 73/24.01 |
| 5,932,793 | A |   | 8/1999 | Dayton et al. ............. 73/24.05 |
| 6,047,589 | A |   | 4/2000 | Hammond et al. ........ 73/24.01 |
| 6,065,328 | A | * | 5/2000 | Dayton et al. ............. 73/25.01 |
| 6,076,392 | A | * | 6/2000 | Drzewiecki .................. 73/23.2 |
| 6,209,387 | B1 | * | 4/2001 | Savidge ..................... 73/24.05 |
| 6,286,360 | B1 |   | 9/2001 | Drzewiecki ................ 73/24.01 |

FOREIGN PATENT DOCUMENTS

| DE | 198 23 193 A1 | 11/1999 | ............ G01N/9/00 |
| EP | 1 063 525 A2 | 7/1999 | .......... G01N/33/22 |
| EP | 0 939 317 A2 | 9/1999 | .......... G01N/33/22 |
| EP | 0 959 354 A2 | 11/1999 | .......... G01N/33/22 |
| WO | 93/08457 | 4/1993 | ............ G01N/9/00 |
| WO | 99/10740 | 3/1999 | .......... G01N/33/22 |

OTHER PUBLICATIONS

International Search Report PCT/US01/12217, Mailed Nov. 13, 2001.
International Preliminary Examination Report PCT/US01/12217, Jul. 8, 2002.
Wild, K.R., "Controlling Processes that are Sensitive to Natural Gas Quality", presented at the 21st World Gas Conference, Nice France, Jun. 6–9, 2000.

(List continued on next page.)

*Primary Examiner*—John Barlow
*Assistant Examiner*—Xiuqin Sun
(74) *Attorney, Agent, or Firm*—Baker Botts L.L.P.

(57) ABSTRACT

A methods of indirectly measuring the nitrogen concentration in a gas mixture. The molecular weight of the gas is modeled as a function of the speed of sound in the gas, the diluent concentrations in the gas, and constant values, resulting in a model equation. Regression analysis is used to calculate the constant values, which can then be substituted into the model equation. If the speed of sound in the gas is measured at two states and diluent concentrations other than nitrogen (typically carbon dioxide) are known, two equations for molecular weight can be equated and solved for the nitrogen concentration in the gas mixture.

10 Claims, 1 Drawing Sheet

| GAS MIXTURE CHARACTERISTIC | RANGE OF GAS MIXTURE CHARACTERISTIC |
|---|---|
| MOLECULAR WEIGHT, $M$ [LBM/LB-MOL] | 16.33 - 19.52 |
| IDEAL SPECIFIC GRAVITY, $G_{id}$ [$M$/28.9625] | 0.564 - 0.674 |
| STANDARD VOLUMETRIC HEATING VALUE $H_{v,std}$ [BTU/REAL SCF AT 60°F, 14.73 PSIA] | 987 - 1150 |
| $C_6$+ CONCENTRATION [mol %] | 0.0009 - 0.100 |
| TOTAL DILUENT CONCENTRATION [mol %] | 0.968 - 7.40 |
| METHANE [mol %] | 83.42 - 98.27 |
| ETHANE [mol %] | 0.516 - 9.53 |
| PROPANE [mol %] | 0.161 - 3.57 |
| ISO-BUTANE [mol %] | 0.0355 - 0.647 |
| N-BUTANE [mol %] | 0.0237 - 0.432 |
| ISO-PENTANE [mol %] | 0.0094 - 0.167 |
| N-PENTANE [mol %] | 0.0063 - 0.112 |
| N-HEXANE [mol %] | 0.0003 - 0.0654 |
| N-HEPTANE [mol %] | 0.0000 - 0.0260 |
| N-OCTANE [mol %] | 0.0000 - 0.0235 |
| CARBON DIOXIDE [mol %] | 0.0330 - 6.00 |
| NITROGEN [mol %] | 0.0330 - 6.00 |

OTHER PUBLICATIONS

U.S. Pending Continuation–in–Part patent application Ser. No. 10/237,492 entitled "A System and Method to Determine Thermophysical Properties of a Multi–Component Gas at Arbitrary Temperature and Pressure", filed by Thomas B. Morrow et al., filed Sep. 9, 2002.

U.S. Pending Continuation–in–Part patent application Ser. No. 10/460,579 entitled "Indirect Measurement of Nitrogen in a Multi–Component Natural Gas by Heating the Gas", filed by Thomas B. Morrow et al., filed Jun. 12, 2003.

* cited by examiner

FIG. 1

| GAS MIXTURE CHARACTERISTIC | RANGE OF GAS MIXTURE CHARACTERISTIC |
|---|---|
| MOLECULAR WEIGHT, $M$ [LBM/LB-MOL] | 16.33 - 19.52 |
| IDEAL SPECIFIC GRAVITY, $G_{id}$ [$M$/28.9625] | 0.564 - 0.674 |
| STANDARD VOLUMETRIC HEATING VALUE $H_{v,std}$ [BTU/REAL SCF AT 60°F, 14.73 PSIA] | 987 - 1150 |
| $C_6+$ CONCENTRATION [mol %] | 0.0009 - 0.100 |
| TOTAL DILUENT CONCENTRATION [mol %] | 0.968 - 7.40 |
| METHANE [mol %] | 83.42 - 98.27 |
| ETHANE [mol %] | 0.516 - 9.53 |
| PROPANE [mol %] | 0.161 - 3.57 |
| ISO-BUTANE [mol %] | 0.0355 - 0.647 |
| N-BUTANE [mol %] | 0.0237 - 0.432 |
| ISO-PENTANE [mol %] | 0.0094 - 0.167 |
| N-PENTANE [mol %] | 0.0063 - 0.112 |
| N-HEXANE [mol %] | 0.0003 - 0.0654 |
| N-HEPTANE [mol %] | 0.0000 - 0.0260 |
| N-OCTANE [mol %] | 0.0000 - 0.0235 |
| CARBON DIOXIDE [mol %] | 0.0330 - 6.00 |
| NITROGEN [mol %] | 0.0330 - 6.00 |

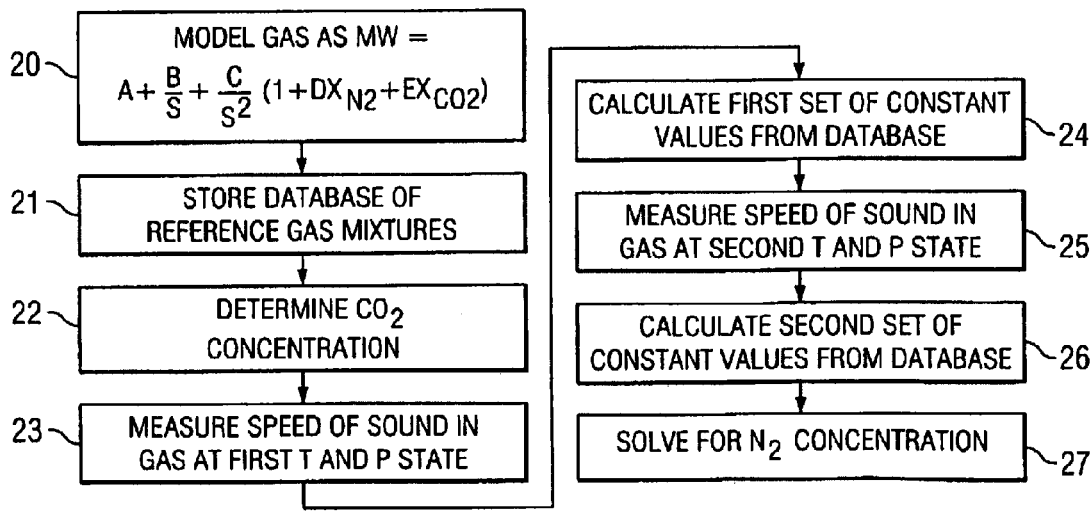

FIG. 2

INDIRECT MEASUREMENT OF NITROGEN IN A MULTI-COMPONENT GAS BY MEASURING THE SPEED OF SOUND AT TWO STATES OF THE GAS

RELATED APPLICATION

This application is a continuation-in-part from U.S. patent application Ser. No. 09/550,431, filed Apr. 17, 2000 and entitled "System and Method to Determine Thermophysical Properties of a Multi-Component Gas" now U.S. Pat. No. 6,604,051.

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

FIELD OF THE INVENTION

This invention relates to the field of measuring constituent components of gas mixtures, and more particularly, to measuring the concentration of nitrogen in a gas mixture.

DESCRIPTION OF THE RELATED ART

The concentration of nitrogen in a gas mixture is difficult to measure directly. Nitrogen has low infrared absorption characteristics, which makes infrared sensing methods difficult. Also, it is chemically inert, which makes electrochemical sensing methods difficult.

Yet, it is often desired to determine the amount of nitrogen in a particular gas mixture. For example, in a natural gas, nitrogen is a diluent and the amount of nitrogen affects heating value. Experimentation has indicated that a plus or minus shift of 0.075 mole % in nitrogen concentration will produce a plus or minus shift of 1.0 BTU/SCF in standard volumetric heating value.

U.S. patent application Ser. No. 09/550,431, entitled "System and Method to Determine Thermophysical Properties of a Multi-Component Gas" and U.S. patent application Ser. No. 10/237,492 entitled "A System and Method to Determine Thermophysical Properties of a Multi-Component Gas at Arbitrary Temperature and Pressure", to K. Behring and T. Morrow, describe inferential methods for deriving the heating value of natural gas. These methods developed from correlation studies of the heating value of a large number of representative samples of natural gas and three independent physical parameters associated with the gas, namely, the speed of sound at specified pressure and temperature and the fractional concentrations of two diluent gas components (carbon dioxide and molecular nitrogen).

U.S. patent application Ser. No. 09/550,431 further describes various methods for determining the amount of molecular nitrogen in a natural gas sample. These methods are inferential in nature in that the concentration of nitrogen in representative natural gas mixtures, like the gas heating value, is correlated with the speed of sound and the carbon dioxide concentration at two independent thermodynamic states. One inferential nitrogen measurement technique is further described in U.S. patent application Ser. No. 10/371,419 entitled "Indirect Measurement of Nitrogen in a Multi-Component Natural Gas by Heating the Gas", a continuation-in-part of U.S. patent application Ser. No. 09/550,431.

BRIEF DESCRIPTION OF THE FIGURES

FIG. 1 illustrates the characteristics of an example of a database for correlating molecular weight of natural gas to the speed of sound in the gas.

FIG. 2 illustrates a method of determining the nitrogen concentration in a gas mixture in accordance with the invention.

DETAILED DESCRIPTION OF THE PREFERRED EMBODIMENT

As stated in the Background, U.S. patent application Ser. No. 09/550,431, entitled "System and Method to Determine Thermophysical Properties of a Multi-Component Gas" and U.S. patent application Ser. No. 10/237,492 entitled "A System and Method to Determine Thermophysical Properties of a Multi-Component Gas at Arbitrary Temperature and Pressure", describe methods for inferentially measuring heating value and energy flow rates of natural gas. U.S. patent application Ser. No. 09/550,431 further describes methods for inferentially measuring nitrogen. One of the nitrogen measurement methods is further described in U.S. patent application Ser. No. 10/371,419 entitled "Indirect Measurement of Nitrogen in a Multi-Component Natural Gas by Heating the Gas". These patent applications are incorporated by reference herein.

One aspect of the above-described methods is correlation of the speed of sound in the gas to the molecular weight of the gas. The calculations for determining the molecular weight require known values for the diluent concentrations in the gas, such as carbon dioxide and nitrogen, as well as known values for the speed of sound, temperature, and pressure. However, there is no need for other constituent values to be known.

For purposes of this description, the gas mixture is assumed to be a natural gas, whose primary diluent components are carbon dioxide and nitrogen. For natural gases, the method is most accurate when the concentration of other diluent gases is low. The method described herein may be extended to other gases containing nitrogen, if those gases behave similarly to natural gases.

It is assumed that for the particular gas mixture in question, the speed of sound in the gas and the concentration of carbon dioxide are known or measurable by direct or indirect measurement. The variables, $X_{CO2}$, $X_{N2}$, and S represent the carbon dioxide concentration, nitrogen concentration, and speed of sound in the gas, respectively. Temperature and pressure of the gas are represented by T and P. Typically, these measurements are made using a finite gas sample.

The molecular weight of a natural gas mixture of unknown composition is constant for the specific mixture. However, the molecular weight is quantitatively unknown because the gas constituents are not known.

As explained in U.S. patent application Ser. No. 09/550,431, molecular weight of a mixture plots semi-linear with sound speed, with the scatter in the data (about 1%) being a function of the diluent concentrations. Molecular weight may be represented by the following equation, which relates molecular weight to speed of sound and the diluent gas concentrations:

$$MW = (A + B/S + C/S^2) * (1 + D*X_{CO2} + E*X_{N2})$$

, where MW is the molecular weight of a gas sample.

The constants A, B, C, D, and E are derived from a database containing reference gas mixtures, whose molecular weights are known. These constants are functions of the gas temperature and pressure, but they are not functions of the gas composition.

FIG. 1 summarizes a database composition range for a set of reference gas compositions. U.S. patent Ser. No. 09/550, 431, incorporated by reference above, provides an example of a suitable database, representing 102 unique gas compositions that fall within these ranges. For each reference gas mixture, the speed of sound can be calculated for a matrix of temperature and pressure values. These speed of sound calculations may be performed using commercially available computer software such as SONICWARE, manufactured by Lomic, Inc. By applying statistical methods to the database, values of the constants can be calculated for any given temperature and pressure state.

The database for producing the constant values may also comprise a smaller set of reference gas compositions, selected to be representative of different molecular weights and diluent concentrations. For example, a database of nine reference gas mixtures might comprise three categories of mixtures, one with high molecular weight, one with intermediate molecular weight, and one with low molecular weight. Each category could then comprise three mixtures, such as, one with no diluents, one with nitrogen as the only diluent, and one with carbon dioxide as the only diluent. An example of a suitable diluent concentration for this database would be 2.0 mole % of either nitrogen or carbon dioxide or both. Once a suitable set of reference gases is selected, standard matrix operations for solving algebraic equations can be used to produce values for the constants. For example, the database might comprise nine reference gases, each having a unique value of molecular weight. The sound speeds for each of the nine gases for a range of discrete temperature and pressure values is calculated and stored. As stated above, this calculation can be performed using commercially available software. Then, once the temperature and pressure of the subject natural gas is measured, interpolation can be used to estimate the speed of sound at that state for the reference gases. With nine values of sound speed, nine values of molecular weight, and nine values of CO2 and N2 for the nine reference gases, there is sufficient information to find the values of A, B, C, D and E at that state. As an alternative to storing pre-calculated sound speed values, the sound speeds for the reference gases could be calculated "on the fly" for the measured temperature and pressure, if appropriate programming is incorporated into the run time calculations.

FIG. 2 illustrates a method of indirectly measuring the nitrogen concentration in a gas mixture in accordance with the invention.

Step 20 is storing a database representing a number of gas mixtures whose diluent constituents are known. Step 21 is modeling the molecular weight as a function of the speed of sound in the gas, as described above. Step 22 is determining the carbon dioxide concentration in the gas, if not already known.

Step 23 is measuring the speed of sound in the gas mixture at a first pressure and temperature condition. At that state, the equation for molecular weight is:

$$MW=(A_1+B_1/S_1+C_1/S_1^2)* (1+D_1*X_{CO2}+E_1*X_{N2})$$

In Step 24, values for the constants are calculated from the database.

In Step 25, the speed of sound measurement is then repeated at a different state. The molecular weight is then expressed as:

$$MW=(A_2+B_2/S_2+C_2/S_2^2)* (1+D_2*X_{CO2}+E_2*X_{N2})$$

Step 26 is recalculating the constants, to obtain a new set of constant values at that state.

The second speed of sound measurement can be at a different pressure or temperature or both, as compared to the first speed of sound measurement. A change in either temperature or pressure or both fulfills the requirement that a measurement be made at a different thermodynamic state. If the two states are too close together, especially in pressure, the constants become closer in value and the nitrogen value less determinate.

One of the speed of sound measurements can be at standard temperature and pressure. This speed of sound measurement is referred to as the "standard sound speed", where standard temperature is 60° F. and standard pressure is 14.73 psia.

In Step 27, it is recognized that the two preceding equations are independent equations for molecular weight, and can be equated to each other to eliminate molecular weight. The resulting equation can then be solved for the concentration of nitrogen:

$$X_{N2} = \frac{\left(A_2 + \frac{B_2}{S_2} + \frac{C_2}{S_2^2}\right)(1 + D_2 X_{CO2}) - \left(A_1 + \frac{B_1}{S_1} + \frac{C_1}{S_1^2}\right)(1 + D_1 X_{CO2})}{E_1\left(A_1 + \frac{B_1}{S_1} + \frac{C_1}{S_1^2}\right) - E_2\left(A_2 + \frac{B_2}{S_2} + \frac{C_2}{S_2^2}\right)}$$

In sum, the above method calls for measurement of pressure, temperature, carbon dioxide concentration, and speed of sound. Because measurements are required at two thermodynamic states, some means is needed to control temperature or pressure. As stated above, typically, the measurements are made to a sample of the gas. For example, a speed of sound sensor may have a chamber containing the sample and means to measure temperature and pressure.

When calculating the constant values, experimentation may indicate that it is desirable to treat the constant values as functions of sound speed. In this case, the constant values D and E above could be refined and expressed as:

$$D=D_0+D_1/S+D_2/S^2$$

$$E=E_0+E_1/S+E_2/S^2$$

Various methods of using reference gas mixtures to obtain constant values by relating molecular weight to speed of sound are further described in U.S. patent application Ser. No. 09/550,431.

What is claimed is:

1. A method of determining the nitrogen concentration in a gas mixture whose carbon dioxide concentration is known, comprising the steps of:

storing a database representing a number of gas mixtures whose molecular weights and carbon dioxide and nitrogen concentrations are known;

modeling the molecular weight of a gas mixture as a function of the speed of sound in the gas mixture, the carbon dioxide concentration, and the nitrogen concentration, and a set of constant values, thereby obtaining a model equation;

at a first temperature and pressure state of the gas mixture: measuring the speed of sound in the gas mixture, determining the constant values for the gas mixture from the database, and substituting these values into the model equation, thereby obtaining a first equation for the molecular weight of the gas;

at a second temperature and pressure state of the gas mixture: measuring the speed of sound in the gas mixture, determining the constant values for the gas mixture from the database, and substituting these values into the model equation, thereby obtaining a second equation for the molecular weight of the gas; and solving the two equations for the nitrogen content of the gas mixture.

2. The method of claim 1, wherein storing step is performed by storing a table of molecular weight and speed of sound values at various states, and the constant values are determined by interpolating that data.

3. The method of claim 1, wherein the primary diluents in the gas mixture are carbon dioxide and nitrogen.

4. The method of claim 1, wherein the gas mixture is a natural gas.

5. The method of claim 1, wherein at least one of the states is standard temperature and pressure.

6. The method of claim 1, wherein the model equation is expressed as:

$$MW=(A+B/S+C/S^2)*(1+D*X_{CO2}+E*X_{N2}).$$

7. The method of claim 1, wherein the constant values D and E are further expressed as:

$$D=D_0+D_1/S+D_2/S^2 \text{ and } E=E_0+E_1/S+E_2/S^2.$$

8. The method of claim 1, wherein the constants are determined by storing pre-calculated speed of sound values for the reference gases for a range of temperature and pressure values, and applying statistical methods to the stored values.

9. The method of claim 1, wherein the constants are determined by storing pre-calculated speed of sound values for the reference gases for a range of temperature and pressure values, interpolating the data to determine speed of sound at a given state, substituting molecular weight, speed of sound, and diluent concentration values into the model equation for each of the reference gases, and solving the resulting system of equations for the constant values.

10. The method of claim 1, wherein the constants are determined by calculating speed of sound values for the reference gases for the measured temperature and pressure values, substituting molecular weight, speed of sound, and diluent concentration values into the model equation for each of the reference gases, and solving the resulting system of equations for the constant values.

* * * * *